(12) United States Patent
Shi et al.

(10) Patent No.: US 8,767,910 B2
(45) Date of Patent: Jul. 1, 2014

(54) HYBRID MULTI-ROW DETECTOR AND FLAT PANEL IMAGING SYSTEM

(75) Inventors: Shuanghe Shi, Southborough, MA (US); Jason R. Chandonnet, Tyngsboro, MA (US); Matthew G. Mooney, Westford, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 273 days.

(21) Appl. No.: 13/166,070

(22) Filed: Jun. 22, 2011

(65) Prior Publication Data

US 2012/0328072 A1 Dec. 27, 2012

(51) Int. Cl.
*A61B 6/03* (2006.01)

(52) U.S. Cl.
USPC .......................................... 378/19

(58) Field of Classification Search
USPC ............. 378/19, 89, 253, 193, 195, 196, 197, 378/198, 17
See application file for complete search history.

(56) References Cited

U.S. PATENT DOCUMENTS

| | | | |
|---|---|---|---|
| 6,940,941 B2 | 9/2005 | Gregerson et al. | |
| 7,001,045 B2 * | 2/2006 | Gregerson et al. | 362/253 |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,249,886 B1 * | 7/2007 | Chao et al. | 378/207 |
| 7,298,814 B2 * | 11/2007 | Popescu | 378/9 |
| 2007/0165783 A1 * | 7/2007 | Abu Tabanjeh | 378/116 |
| 2009/0110141 A1 * | 4/2009 | Stayman | 378/19 |
| 2010/0290690 A1 | 11/2010 | Hartmann et al. | |
| 2011/0080993 A1 * | 4/2011 | Hoffman et al. | 378/19 |
| 2012/0177173 A1 * | 7/2012 | Xu et al. | 378/19 |

FOREIGN PATENT DOCUMENTS

WO  WO-03103496 A1  12/2003
WO  WO-2012177863 A2  12/2012

OTHER PUBLICATIONS

French Hospital Medical Center News Release. New GPS Technology Aids in Radiology Procedures at French Hospital. Sep. 16, 2010. http://www.veranmedical.com/Resources/IG4-French%20Hospital-San%20Luis%20Obispo.pdf.*
K Marten, C Dullin, W Machann, J S Schmid, M Das, K-P Hermann, and C. Engelke. Comparison of flat-panel-detector-based CT and multidetector row CT in automated volumetry of pulmonary nodules using an anthropomorphic chest phantom. The British Journal of Radiology, 82 (2009), 716-723.*

(Continued)

*Primary Examiner* — Irakli Kiknadze
(74) *Attorney, Agent, or Firm* — Harness, Dickey

(57) ABSTRACT

A system and a method for acquiring image data of a subject with an imaging system are provided. The system can include a gantry that completely annularly encompasses at least a portion of the subject, and a source positioned within the gantry. The source can be responsive to a signal to output at least one pulse. The system can include a multi-row detector positioned within the gantry. The multi-row detector can be in alignment with the source and sets multi-row detector data based on the detected at least one signal. The system can include a flat panel detector positioned within the gantry. The flat panel detector can in alignment with the source and sets flat panel detector data based on the detected at least one signal. The system can include an image acquisition control module that determines which of the multi-row detector and the flat panel detector to use.

25 Claims, 9 Drawing Sheets

(56) References Cited

OTHER PUBLICATIONS

Invitation to Pay Additional Fees mailed Dec. 18, 2012 for PCT/US2012/043530 claiming benefit of U.S. Appl. No. 13/166,070, filed Jun. 22, 2011.
International Search Report and Written Opinion mailed Feb. 26, 2013 for PCT/US2012/043530 claiming benefit of U.S. Appl. No. 13/166,070, filed Jun. 22, 2011.
"Medtronic O-Arm Multi-Dimensional Surgical Imaging System"; Brochure, 24pp, 2009.
Collimare® Engineering Services. Collimator designs. (2008) http://www.collimare.net/enqineeringServices.asp. Web accessed Mar. 21, 2012. 1 page.
International Preliminary Report on Patentability and Written Opinion mailed Jan. 9, 2014 for PCT/US2012/043530 claiming benefit of U.S. Appl. No. 13/166,070, filed Jun. 22, 2011.

* cited by examiner

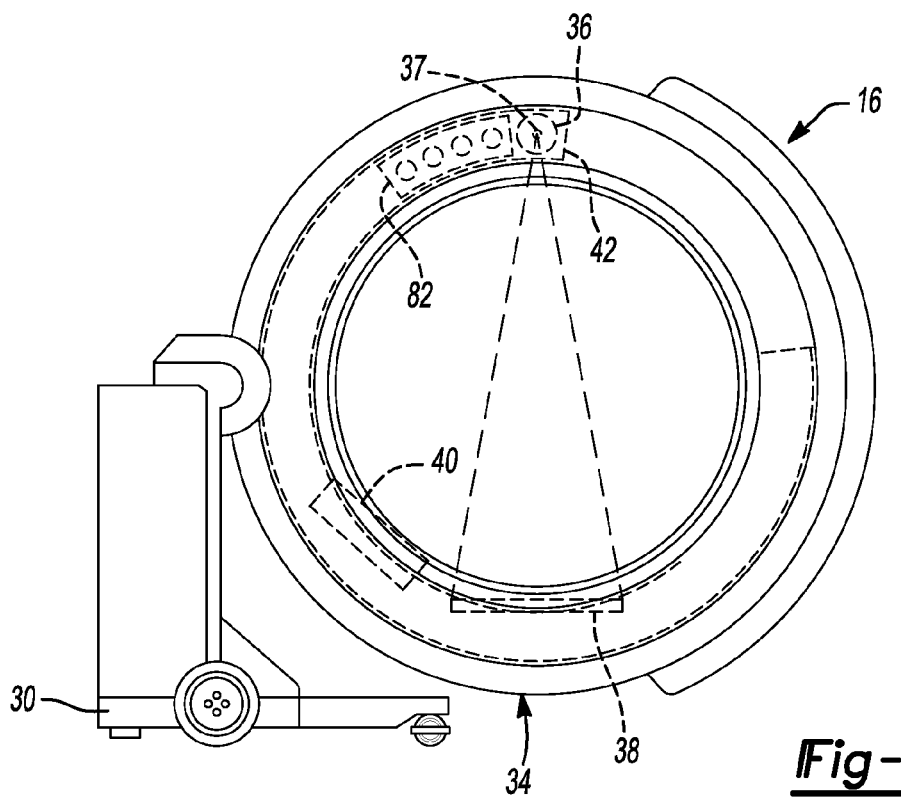
_Fig-4A_
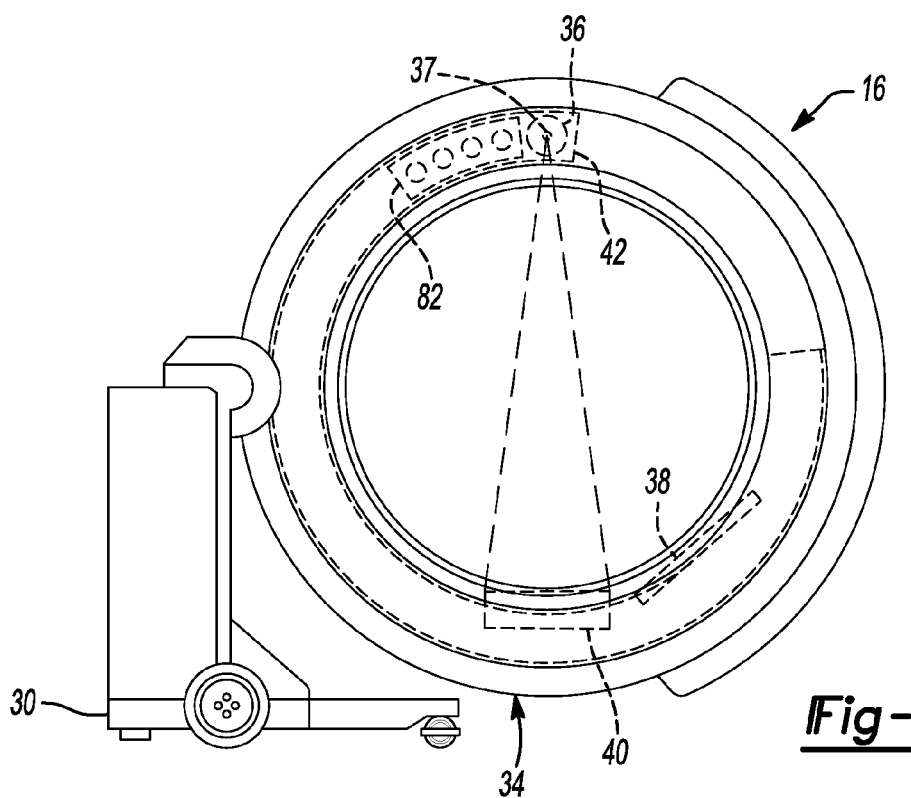
_Fig-4B_

HYBRID MULTI-ROW DETECTOR AND FLAT PANEL IMAGING SYSTEM

FIELD

The present disclosure relates to imaging a subject, and particularly to generating an image of subject using an imaging system having a multi-row detector and a flat panel detector.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

According to various embodiments, provided is a system for acquiring image data of a subject with an imaging system. The system can include a gantry that completely annularly encompasses at least a portion of the subject, and a source positioned within and movable relative to the gantry. The source can be responsive to a signal to output at least one pulse. The system can include a multi-row detector positioned within and movable relative to the gantry. The multi-row detector can be positionable into alignment with the source to detect the at least one pulse emitted by the source and set multi-row detector data based on the detected at least one signal. The system can include a flat panel detector positioned within and movable relative to the gantry. The flat panel detector can be positionable into alignment with the source to detect the at least one pulse emitted by the source and set flat panel detector data based on the detected at least one signal. The system can include an image acquisition control module that sets the signal for the source and determines which of the multi-row detector and the flat panel detector to use to detect the at least one pulse emitted by the source.

Further provided is a method for acquiring image data of a subject with an imaging system. The method can include providing a gantry operable to completely annularly encompass at least a portion of the subject, the imaging system including a source, a multi-row detector and a flat panel detector positioned within and coupled to a rotor movable relative to the gantry. The method can include receiving at least one user input that provides a request for acquiring image data of a portion of the subject, and determining, based on the user input, which of the multi-row detector and the flat panel detector to use to acquire the image data. The method can also include moving the selected one of the multi-row detector and flat panel detector into alignment with the source, and outputting at least one pulse with the source. The method can include receiving the at least one pulse with the selected one of the multi-row detector and the flat panel detector, and outputting, based on the at least one pulse received by the detector, an image of the subject.

Also provided is a method for acquiring image data of a subject with an imaging system. The method can include providing a gantry operable to completely annularly encompass at least a portion of the subject, the imaging system including a source, a multi-row detector and a flat panel detector positioned within and coupled to a rotor movable relative to the gantry. The method can include receiving at least one user input that provides a request for acquiring image data of a portion of the subject, and determining, based on the user input, whether to use high contrast image acquisition or low contrast image acquisition to acquire the image data. The method can also include moving the multi-row detector into alignment with the source to perform the low contrast image acquisition, and moving the flat panel detector into alignment with the source to perform the high contrast image acquisition. The method can include outputting at least one pulse with the source, and receiving the at least one pulse with the selected one of the multi-row detector and the flat panel detector. The method can also include reconstructing, based on the at least one pulse received by the detector, an image of the subject, and displaying the reconstructed image of the subject on a display.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4A is a schematic illustration of a source of the imaging system of FIG. 1 aligned with the multi-row detector;

FIG. 4B is a schematic illustration of a source of the imaging system of FIG. 1 aligned with the flat panel detector;

DETAILED DESCRIPTION

Figure 1:
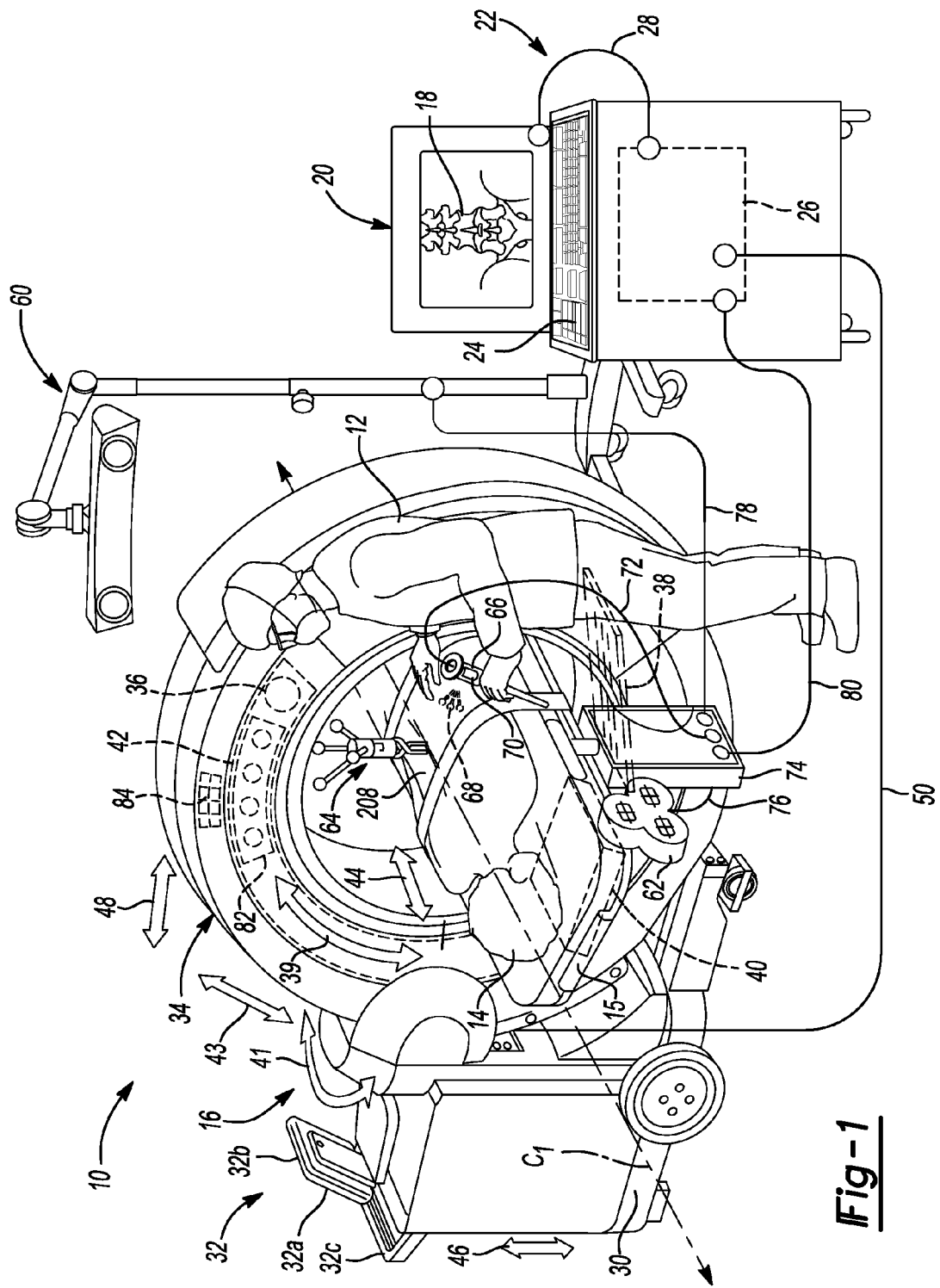
FIG. 1 is an environmental view of an exemplary imaging system in an operating theatre, including a multi-row detector and a flat panel detector according to various embodiments.

The following description is merely exemplary in nature. It should be understood that throughout the drawings, corresponding reference numerals indicate like or corresponding parts and features. As indicated above, the present teachings are directed toward an imaging device, such as an O-Arm® imaging system sold by Medtronic Navigation, Inc. having a place of business in Louisville, Colo., USA. It should be noted, however, that the present teachings could be applicable to any appropriate imaging device, such as a C-arm imaging device. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

With reference to FIG. 1, in an operating theatre or operating room 10, a user, such as a user 12, can perform a procedure on a patient 14. In performing the procedure, the user 12 can use an imaging system 16 to acquire image data of the patient 14 for performing a procedure. The image data acquired of the patient 14 can include two-dimension (2D) projections acquired with an x-ray imaging system, including those disclosed herein. It will be understood, however, that 2D forward projections of a volumetric model can also be generated, also as disclosed herein.

In one example, a model can be generated using the acquired image data. The model can be a three-dimension (3D) volumetric model generated based on the acquired image data using various techniques, including algebraic iterative techniques, also as discussed further herein. Displayed image data 18 can be displayed on a display device 20, and additionally, could be displayed on a display device 32a associated with an imaging computing system 32, as will be discussed in greater detail herein. The displayed image data 18 can be a 2D image, a 3D image, or a time changing four-dimension image. The displayed image data 18 can also include the acquired image data, the generated image data, both, or a merging of both the types of image data.

It will be understood that the image data acquired of the patient 14 can be acquired as 2D projections, for example with an x-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a computing system 22. The computing system 22 can include a variety of computer-readable media. The computer-readable media can be any available media that can be accessed by the computing system 22 and can include both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can comprise any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 could comprise a touchpad or tablet computing device, and further, that the computing system 22 could be integrated within or be part of the imaging computing system 32 associated with the imaging system 16. A connection 28 can be provided between the computing system 22 and the display device 20 for data communication to allow driving the display device 20 to illustrate the image data 18.

The imaging system 16 can include the O-Arm® imaging system sold by Medtronic Navigation, Inc. having a place of business in Louisville, Colo., USA. The imaging system 16, including the O-Arm® imaging system, or other appropriate imaging systems in use during a selected procedure are also described in U.S. patent application Ser. No. 12/465,206, entitled "System And Method For Automatic Registration Between An Image And A Subject," filed on May 13, 2009, U.S. Publication No. 2010-0290690, incorporated herein by reference. Additional description regarding the O-Arm imaging system or other appropriate imaging systems can be found in U.S. Pat. Nos. 7,188,998, 7,108,421, 7,106,825, 7,001,045 and 6,940,941, each of which is incorporated herein by reference.

The O-Arm® imaging system 16 can include a mobile cart 30 that includes the imaging computing system 32 and an imaging gantry 34 in which is positioned a source 36, a collimator 37, a multi-row detector 38, a flat panel detector 40 and a rotor 42. With reference to FIG. 1, the mobile cart 30 can be moved from one operating theater or room to another and the gantry 34 can move relative to the mobile cart 30, as discussed further herein. This allows the imaging system 16 to be mobile so that it can be used in multiple locations and with multiple procedures without requiring a capital expenditure or space dedicated to a fixed imaging system.

With continued reference to FIG. 1, the gantry 34 can define an isocenter of the imaging system 16. In this regard, a centerline C1 through the gantry 34 can define an isocenter or center of the imaging system 16. Generally, the patient 14 can be positioned along the centerline C1 of the gantry 34, so that a longitudinal axis of the patient 14 can be aligned with the isocenter of the imaging system 16.

Figure 2:
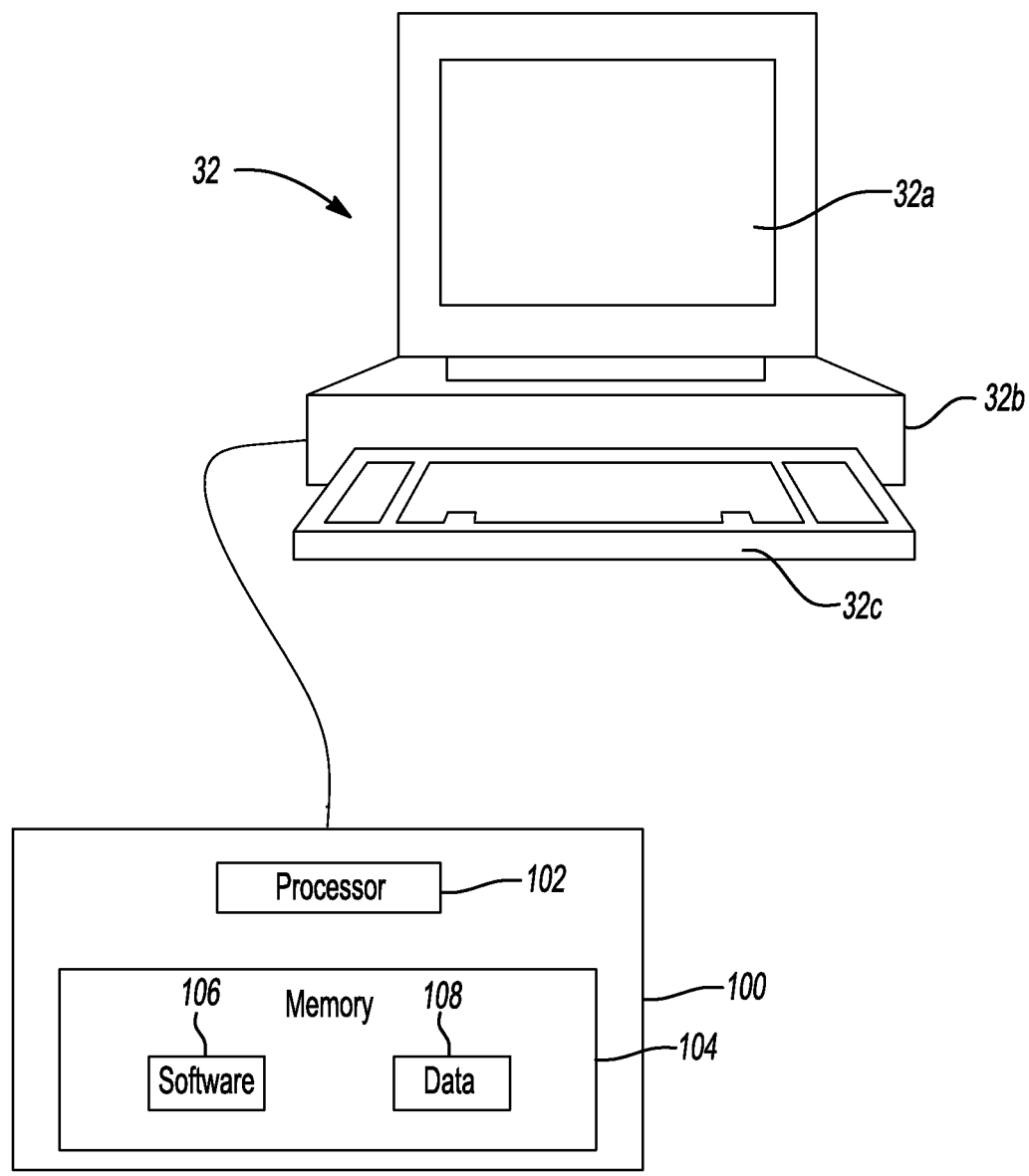
FIG. 2 is a schematic illustration of an exemplary computing system for use with the imaging system of FIG. 1

With reference to FIG. 2, a diagram is provided that illustrates an exemplary embodiment of the imaging computing system 32, some or all of the components of which can be used in conjunction with the teachings of the present disclosure. The imaging computing system 32 can include a variety of computer-readable media. The computer-readable media can be any available media that can be accessed by the imaging computing system 32 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 32. The computer-readable media may be accessed directly or through a network such as the Internet.

In one example, the imaging computing system 32 comprises a display device 32a and a system unit 32b. As illustrated, the display device 32a can comprise a computer video screen or monitor. The imaging computing system 32 can also include at least one input device 32c. The system unit 32b includes, as shown in an exploded view at 100, a processor 102 and a memory 104, which can include software 106 and data 108.

In this example, the at least one input device 32c comprises a keyboard. It should be understood, however, that the at least one input device 32c can comprise any suitable device to enable a user to interface with the imaging computing system 32, such as a touchpad, touch pen, touch screen, keyboard, mouse, joystick, trackball, wireless mouse, audible control or a combination thereof. Furthermore, while the imaging computing system 32 is described and illustrated herein as comprising the system unit 32b with the display device 32a, the imaging computing system 32 could comprise a touchpad or tablet computing device or use display device 20.

As will be discussed with regard to FIGS. 5-7, the imaging computing system 32 can control the movement, positioning and adjustment of the multi-row detector 38, the flat panel detector 40 and the rotor 42 independently to enable image data acquisition via an image acquisition control module 110, which can each be stored in the memory 104 and accessed by the processor 102. A connection can be provided between the processor 102 and the display device 32a for data communication to allow driving the display device 32a to illustrate the image data 18.

Briefly, with reference to FIGS. 1 and 3-4B, the source 36 can emit x-rays through the patient 14 to be detected by the multi-row detector 38 or the flat panel detector 40. As is understood by one skilled in the art, the x-rays emitted by the source 36 can be shaped by the collimator 37 and emitted for detection by the multi-row detector 38 (FIG. 4A) or the flat panel detector 40 (FIG. 4B). As is generally known, the collimator 37 can shape the x-rays emitted by the source 36. As the collimator 37 can be commercially available as the Compact Square Field Collimator sold by Collimare Engineering of Wheat Ridge, Colo., USA and included with the O-Arm® imaging system sold by Medtronic Navigation, Inc. of Louisville, Colo., USA, the collimator 37 will not be discussed in great detail herein. Briefly, however, the collimator 37 can include one or more leaves, which can be controlled to shape the x-rays emitted by the source 36. As will be discussed, the collimator 37 can be used to shape the x-rays emitted by the source 36 into a beam that corresponds with the shape of the selected one of the multi-row detector 38 and the flat panel detector 40. The multi-row detector 38 can be selected to acquire image data of low contrast regions of the anatomy, such as regions of soft tissue. The flat panel detector 40 can be selected to acquire image data of high contrast regions of the anatomy, such as bone. The source 36, collimator 37, the multi-row detector 38 and the flat panel detector 40 can each be coupled to the rotor 42.

Figure 3A:
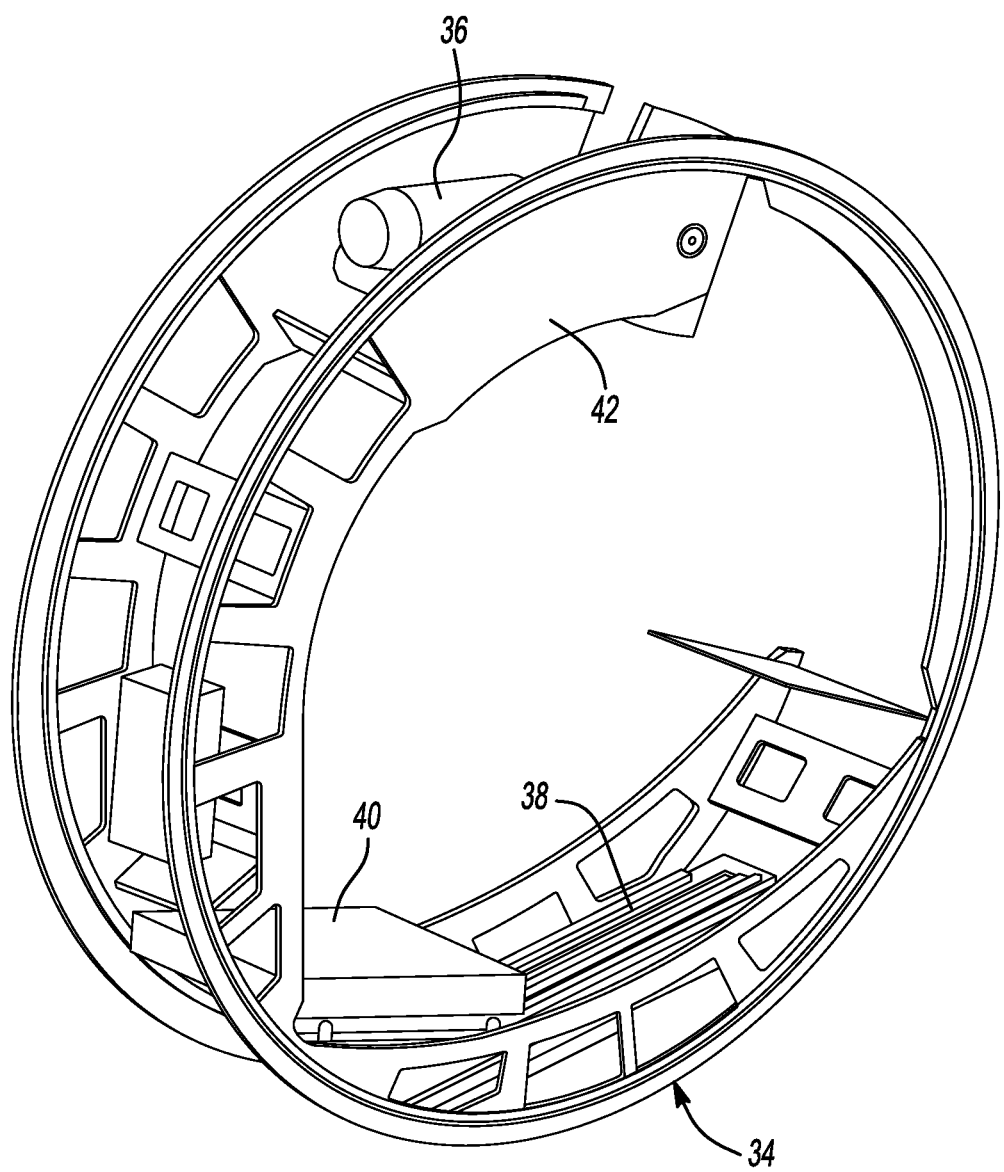
FIG. 3A is a schematic illustration of a gantry of the imaging system of FIG. 1, including a multi-row detector and a flat panel detector according to a first exemplary configuration.
Figure 3B:
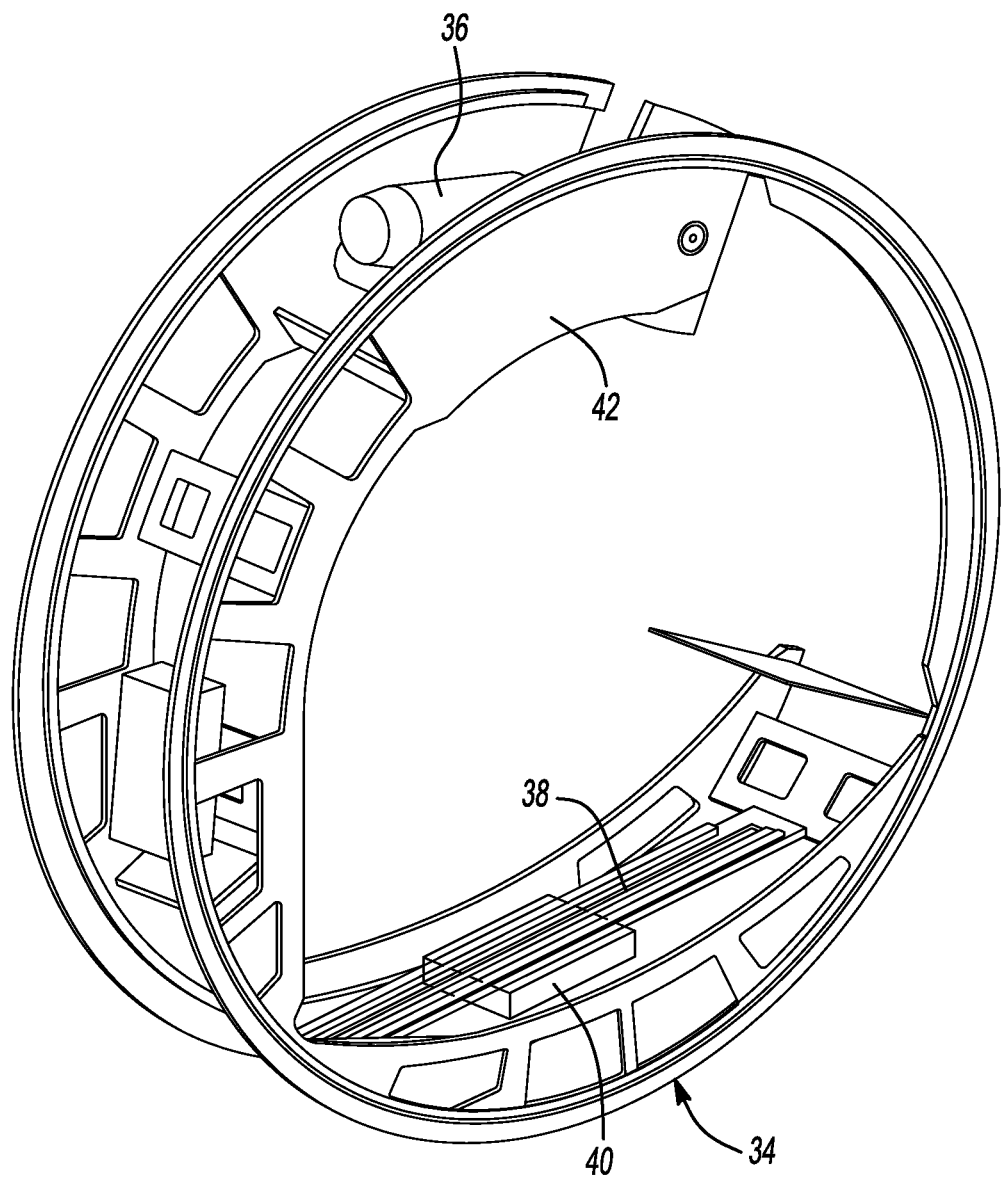
FIG. 3B is a schematic illustration of a gantry of the imaging system of FIG. 1, including a multi-row detector and a flat panel detector according to a second exemplary configuration.

Generally, the multi-row detector 38 and the flat panel detector 40 can be coupled to the rotor 42 so as to be diametrically opposed from the source 36 and the collimator 37 within the gantry 34, and independently movable relative to each other into alignment with the source 36 and the collimator 37 in order to perform a desired imaging procedure. In one example, the multi-row detector 38 can be positioned such that the flat panel detector 40 can be adjacent to the multi-row detector 38 (FIG. 3A). In one alternative example, the flat panel detector 40 can be moved over the multi-row detector 38 into alignment with the source 36 when it is desired to acquire an image using the flat panel detector 40. In another example, the multi-row detector 38 could be positioned over the flat panel detector 40 (FIG. 3B). As a further alternative, the multi-row detector 38 and the flat panel detector 40 could each be separately movable, so that the selected multi-row detector 38 or flat panel detector 40 could be aligned with the source 36 and the collimator 37 for a desired imaging procedure. Generally, the selected one of the multi-row detector 38 and the flat panel detector 40 can be aligned with the source 36 and the collimator 37 when the selected one of the multi-row detector 38 and the flat panel detector 40 is substantially opposite or about 180 degrees apart from the source 36 and the collimator 37.

With reference to FIG. 1, as the source 36, collimator 37, multi-row detector 38 and flat panel detector 40 are coupled to the rotor 42, the source 36, collimator 37, multi-row detector 38 and flat panel detector 40 are movable within the gantry 34 about the patient 14. Thus, the multi-row detector 38 and the flat panel detector 40 can move rotationally in a 360° motion around the patient 14 generally in the directions of arrow 39, and the source 36 and collimator 37 can move in concert with at least one of the multi-row detector 38 and the flat panel detector 40 such that the source 36 and collimator 37 remain generally 180° apart from and opposed to the at least one of the multi-row detector 38 and flat panel detector 40.

The gantry 34 can isometrically sway or swing (herein also referred to as iso-sway) generally in the direction of arrow 41, relative to the patient 14, which can be placed on a patient support or table 15. The gantry 34 can also tilt relative to the patient 14 illustrated by arrows 43, move longitudinally along the line 44 relative to the patient 14 and the mobile cart 30, can move up and down generally along the line 46 relative to the mobile cart 30 and transversely to the patient 14, and move perpendicularly generally in the direction of arrow 48 relative to the patient 14 to allow for positioning of the source 36, collimator 37, multi-row detector 38 and flat panel detector 40 relative to the patient 14.

The O-Arm® imaging system 16 can be precisely controlled by the imaging computing system 32 to move the source 36, collimator 37, the multi-row detector 38 and the flat panel detector 40 relative to the patient 14 to generate precise image data of the patient 14. In addition, the imaging system 16 can be connected with the processor 26 via connection 50 which can include a wired or wireless connection or physical media transfer from the imaging system 16 to the processor 26. Thus, image data collected with the imaging system 16 can also be transferred from the imaging computing system 32 to the computing system 22 for navigation, display, reconstruction, etc.

Briefly, with continued reference to FIG. 1, according to various embodiments, the imaging system 16 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. If desired, the components associated with performing a navigated procedure could be integrated within the imaging system 16. The navigated space or navigational domain relative to the patient 14 can be registered to the image data 18 to allow registration of a navigation space defined within the navigational domain and an image space defined by the image data 18. A patient tracker or a dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74, which can communicate with the electromagnetic localizer 62 and/or the optical localizer 60. Using the communication lines 72, 78 respectively, the navigation interface device 74 can then communicate with the processor 26 with a communication line 80. It will be understood that any of the connections or communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 could be graphically illustrated as an icon superimposed on the image data 18.

Further, the imaging system 16 can include a tracking device, such as an optical tracking device 82 or an electromagnetic tracking device 84 to be tracked with a respective optical localizer 60 or the electromagnetic localizer 62. The tracking device 82, 84 can be associated directly with the source 36, multi-row detector 38, flat panel detector 40, rotor 42, the gantry 34, or other appropriate part of the imaging system 16 to determine the location or position of the source 36, multi-row detector 38, flat panel detector 40, rotor 42 and/or gantry 34 relative to a selected reference frame. As illustrated, the tracking device 82, 84 can be positioned on the exterior of the housing of the gantry 34. Accordingly, the imaging system 16 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206, filed on May 13, 2009.

Figure 5:
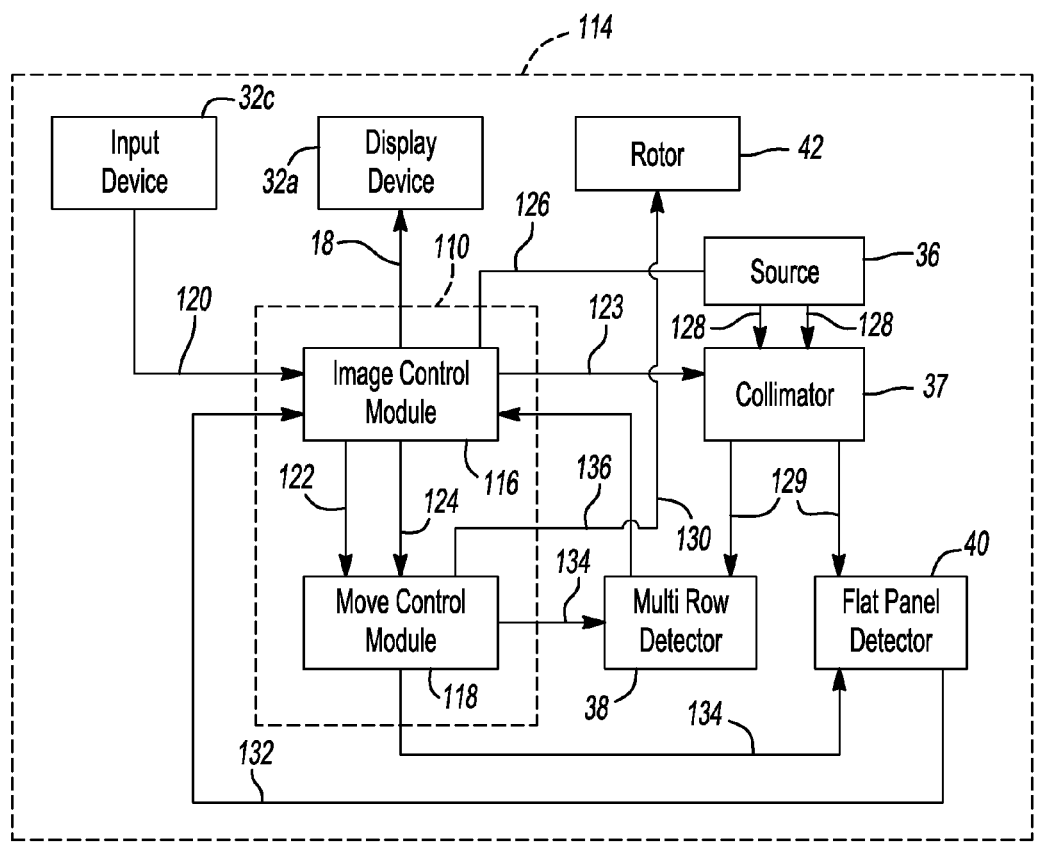
FIG. 5 is a simplified block diagram illustrating a system for implementing an image acquisition control module according to various embodiments.

With reference to FIG. 5, a simplified block diagram schematically illustrates an exemplary system 114 for implementing the image acquisition control module 110 according to various embodiments. In one example, the image acquisition control module 110 can be implemented by the imaging computing system 32 of the imaging system 16. The image acquisition control module 110 can include an image control module 116 and a move control module 118.

The image control module 116 can receive user input data 120 from the input device 32c and can output image data 18 to the display device 32a. Note that while the display device is illustrated and described herein as comprising the display device 32a, the imaging computing system 32 could output image data 18 to the display device 20. The user input data 120 can comprise a request to acquire image data of the patient 14, as will be discussed herein. Based on the user input data 120, the image control module 116 can set a detector signal 122 and a motion signal 124 to the move control module 118. The detector signal 122 can comprise a selected detector for the image acquisition and the motion signal 124 can include a motion profile for the rotor 42 to move to acquire the image data. The image control module 116 can also send a source signal 126 to the source 36. The source signal 126 can comprise a signal for the source 36 to output or emit at least one or more x-ray pulses 128. The image control module 116 can also send a collimator signal 123 to the collimator 37. The collimator signal 123 can comprise a signal that indicates a selected shape of one or more collimated x-ray pulses 129. The selected shape of the collimated x-ray pulses 129 can correspond to the selected one of the multi-row detector 38 and the flat panel detector 40. In this regard, if the multi-row detector 38 is selected, the collimated x-ray pulses 129 can be shaped by the collimator 37 to match the shape of the multi-row detector 38. If the flat panel detector 40 is selected, then the collimated x-ray pulses 129 can be shaped by the collimator 37 to match the shape of the flat panel detector 40.

The image control module 116 can also receive as input a multi-row detector signal 130, which can comprise the one or more collimated x-ray pulses 129 detected by the multi-row detector 38. The image control module 116 can receive as input a flat panel detector signal 132, which can comprise the one or more collimated x-ray pulses 129 detected by the flat panel detector 40. Based on the received collimated x-ray pulses 129, the image control module 116 can generate the image data 18.

In one example, the image data 18 can comprise a single 2D image. In another example, the image control module 116 can perform automatic reconstruction of an initial three dimensional model of the area of interest of the patient 14. Reconstruction of the three dimensional model can be performed in any appropriate manner, such as using algebraic techniques for optimization. Appropriate algebraic techniques include Expectation maximization (EM), Ordered Subsets EM (OS-EM), Simultaneous Algebraic Reconstruction Technique (SART) and total variation minimization. The application to performing a 3D volumetric reconstruction based on the 2D projections allows for efficient and complete volumetric reconstruction.

Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. In this regard, the stylized model can provide additional detail regarding the anatomy of the patient 14, which can enable the user to plan the surgical intervention much more efficiently. The theoretical model can be associated with theoretical image data to construct the theoretical model. In this way, the model or the image data 18 can be built based upon image data acquired of the patient 14 with the imaging system 16. The image control module 116 can output image data 18 to the display device 32*a*.

The move control module 118 can receive as input the detector signal 122 and the motion signal 124 from the image control module 116. Based on the detector signal 122 from the image control module 116, the move control module 118 can set a move signal 134 to move the selected one of the multi-row detector 38 or the flat panel detector 40 into alignment with the source 36 and the collimator 37. Based on the motion signal 124, the move control module 118 can also set a move signal 136 for the rotor 42 to move or rotate the rotor 42 within the gantry 34 relative to the patient 14. Generally, the rotor 42 can move the source 36, the collimator 37, the multi-row detector 38 and the flat panel detector 40 about 360° around the longitudinal axis of the patient 14 within the gantry 34. The movement of the source 36, the collimator 37, the multi-row detector 38 and the flat panel detector 40 about the patient 14 can be optimized to allow the imaging system 16 to acquire image data at a plurality of selected locations and orientations relative to the patient 14.

In this regard, the 2D projection image data can be acquired by substantially annular or 360° orientation movement of the source 36, the multi-row detector 38 and the flat panel detector 40 around the patient 14. Also, due to movements of the gantry 34, the source 36, the multi-row detector 38 and the flat panel detector 40 need never move in a pure circle, but rather can move in a spiral helix, or other rotary movement about or relative to the patient 14. This can reduce the patient's exposure to radiation.

Also, the path can be substantially non-symmetrical and/or non-linear based on movements of the imaging system 16, such as the gantry 34. In other words, the path need not be continuous in that the gantry 34 can stop, move back in the direction from which it just came (e.g., oscillate), etc. in following the optimal path. Thus, the source 36, the collimator 37, the multi-row detector 38 and the flat panel detector 40 need never travel a full 360° around the patient 14 as the gantry 34 may tilt or otherwise move and the source 36, the collimator 37, the multi-row detector 38 and the flat panel detector 40 may stop and move back in the direction it has already passed.

Figure 6:
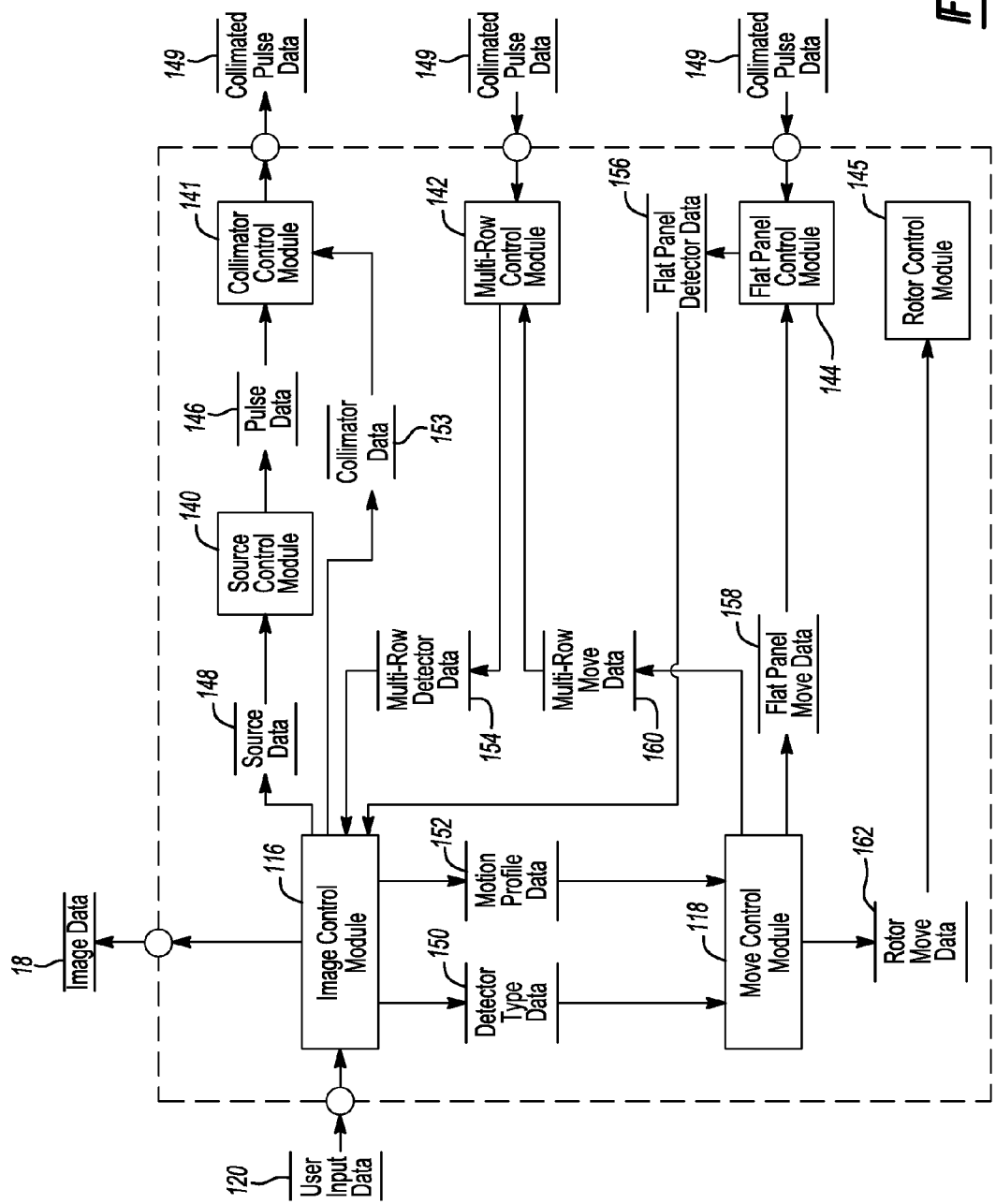
FIG. 6 is a dataflow diagram illustrating an exemplary control system performed by the image acquisition control module of FIG. 5.

With reference to FIG. 6, a dataflow diagram illustrates various components of an image control system that can be embedded within the image acquisition control module 110. The image acquisition control module 110 can control the imaging system 16 to generate the image data 18 for display on the display device 32*a* and/or display device 20. Various embodiments of the image acquisition control system according to the present disclosure can include any number of sub-modules embedded within the image acquisition control module 110. The sub-modules shown may be combined and/or further partitioned to similarly generate the image data 18. Further, the image acquisition control module 110 can comprise one or more software modules embodied in non-transitory, machine readable code that runs on the processor 102. Inputs to the system can be received from the input device 32*c*, input device 24, or even received from other control modules (not shown) within the computing system 22 or imaging computing system 32, and/or determined by other sub-modules (not shown) within the image acquisition control module 110 (not shown).

With continuing reference to FIG. 6, the image acquisition control module 110 can include the image control module 116, the move control module 118, a source control module 140, a collimator control module 141, a multi-row control module 142, a flat panel control module 144 and a rotor control module 145. The image control module 116 can receive as input user input data 120. The user input data 120 can comprise input received from the input device 32*c* or input device 24. The user input data 120 can comprise a request for the imaging system 16 to acquire image data of the patient 14, and can include information as to whether the region of interest on the patient 14 is a high contrast region (e.g. boney tissue) or a low contrast region (e.g. soft tissue). In one example, the user input data 120 can comprise a region of interest on the anatomy, and the image control module 116 can automatically determine to use the multi-row detector 38 or the flat panel detector 40 based on the region of interest. For example, the user can employ the multi-row detector 38 to acquire an image of soft tissue, and the flat panel detector 40 to acquire an image of boney tissue.

Based on the user input data 120, the image control module 116 can set source data 148 for the source control module 140 and can set detector type data 150 for the move control module 118. The image control module 116 can also set motion profile data 152 for the move control module 118 and collimator data 153 for the collimator control module 141. The source data 148 can comprise a signal to output the x-ray pulses 128, or a signal to power-down the imaging system 16. The detector type data 150 can comprise the selected one of the multi-row detector 38 and the flat panel detector 40 to acquire the image data. The motion profile data 152 can comprise a desired profile for the movement of the rotor 42 within the gantry 34. The collimator data 153 can comprise a signal to shape the x-ray pulses 128 into collimated x-ray pulses 129 to match the selected one of the multi-row detector 38 and flat panel detector 40.

The image control module 116 can also receive as input multi-row detector data 154 and flat panel detector data 156. The multi-row detector data 154 can comprise the energy from the collimated x-ray pulses 129 received by the multi-row detector 38. The flat panel detector data 156 can comprise the energy from the collimated x-ray pulses 129 received by the flat panel detector 40. Based on the multi-row detector data 154 and the flat panel detector data 156, the image control module 116 can generate image data 18, and can output this image data 18 to the display device 32*a* or display device 20.

The move control module 118 can receive as input the detector type data 150 and the motion profile data 152. Based on the detector type data 150, the move control module 118 can set flat panel move data 158 or multi-row move data 160. The flat panel move data 158 can comprise a desired position for the flat panel detector 38 to move to in order to be aligned with the source 36 and collimator 37. The multi-row move data 160 can comprise a desired position for the multi-row detector 38 to move in order to be aligned with the source 36 and collimator 37. It should be noted that this dataflow is merely exemplary, as only one of the multi-row detector 38 and the flat panel detector 40 can be movable relative to the other, if desired.

Based on the motion profile data 152, the move control module 118 can set rotor move data 162 for the rotor control module 145. The rotor move data 162 can comprise a desired movement profile for the rotor 42 to move within the gantry 34 to enable the acquisition of the image data.

With continued reference to FIG. 6, the source control module 140 can receive as input the source data 148 from the image control module 116. Based on the source data 148, the source 36 can set pulse data 146 for the collimator control module 141. The pulse data 146 can comprise at least one x-ray pulse 128.

The collimator control module 141 can receive as input the collimator data 153 from the image control module 116 and the pulse data 146 from the source control module 140. Based on collimator data 153, the collimator 37 can shape the pulse data 146 and output collimated pulse data 149 for the selected one of the multi-row detector 38 and flat panel detector 40. The collimated pulse data 149 can comprise at least one collimated x-ray pulse 129.

The multi-row control module 142 can receive as input the multi-row move data 160 and the collimated pulse data 149. Based on the multi-row move data 160, the multi-row detector 38 can move into alignment with the source 36. Based on the received pulse data 146, the multi-row control module 142 can set the multi-row detector data 154 for the image control module 116.

The flat panel control module 144 can receive as input the flat panel move data 158 and the collimated pulse data 149. Based on the flat panel move data 158, the flat panel detector 40 can move into alignment with the source 36. Based on the received pulse data 146, the flat panel control module 144 can set the flat panel detector data 156 for the image control module 116.

The rotor control module 145 can receive as input the rotor move data 162. Based on the rotor move data 162, the rotor 42 can move within the gantry 34 to a desired location in order to acquire the image data.

Figure 7:
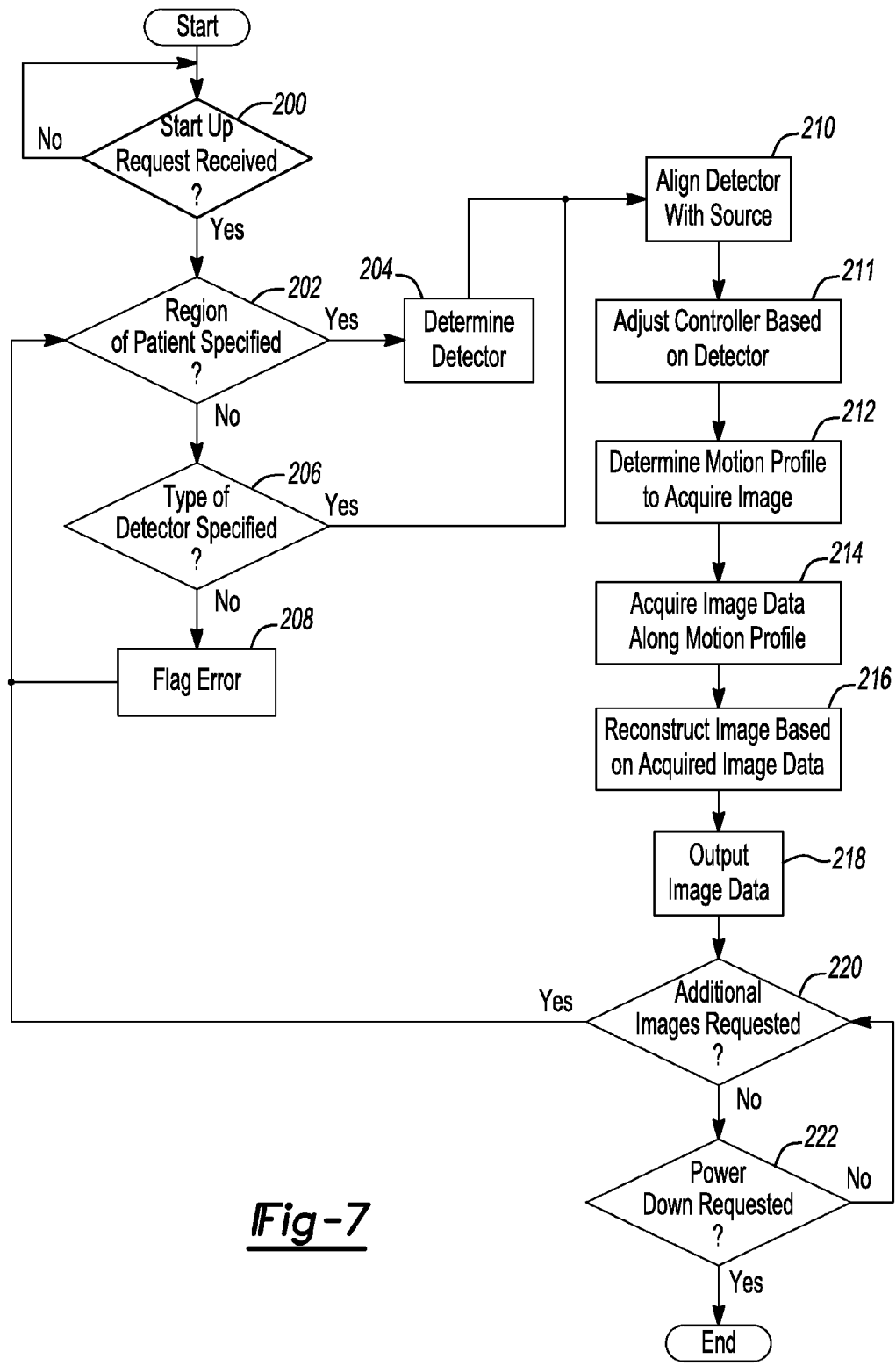
FIG. 7 is a flowchart illustrating an exemplary method performed by the image acquisition control module.

With reference now to FIG. 7, a flowchart diagram illustrates an exemplary method performed by the image acquisition control module 110. It should be noted that the flowchart diagram described herein is merely exemplary, as the imaging system 16 could be in any desired or user requested manner. With continued reference to FIG. 7, at decision block 200, the method determines if a startup request signal has been received via the input device 32c. If not, the method loops. Otherwise, the method goes to block 202.

At decision block 202, the method determines if a region of the patient has been specified for the acquisition of the image. For example, the user input data 120 could comprise a request to gather image data regarding a portion of the patient's spine. In another example, the user input data 120 could comprise a request to gather image data regarding a patient's heart. If the region of the patient is specified, then the method goes to block 204. Otherwise, the method goes to decision block 206. At block 204, the method can determine which of the multi-row detector 38 and the flat panel detector 40 to employ to acquire the requested image data. For example, the multi-row detector 38 can be employed to acquire images of soft tissue, and the flat panel detector 40 can be employed to acquire images of boney tissue. Then, the method goes to block 210.

At decision block 206, the method determines if a type of detector has been specified. For example, if the user input data 120 includes a request to use the multi-row detector 38 or the flat panel detector 40. If the type of detector has not been specified, then the method flags an error at block 208 and loops to decision block 202 to request a region of the patient be input by the user. Otherwise, if the type of detector has been specified, then the method goes to block 210.

At block 210, the method aligns the selected one of the multi-row detector 38 and the flat panel detector 40 with the source 36 and collimator 37. For example, if the multi-row detector 38 is selected, then the multi-row detector 38 can be aligned with the source 36 and collimator 37 such that the multi-row detector 38 is opposed from the source 36 and collimator 37, as shown in FIG. 4A. If the flat panel detector 40 is selected, then the flat panel detector 40 can be aligned with the source 36 and collimator 37 such that the flat panel detector 40 is opposed from the source 36 and collimator 37, as shown in FIG. 4B.

With reference back to FIG. 7, at block 211, the method can adjust the collimator 37 based on the selected one of the multi-row detector 38 and the flat panel detector 40 so that the collimated x-ray pulses 129 can match the selected one of the multi-row detector 38 and the flat panel detector 40. Then, at block 212, the method can determine the motion profile for acquisition of the image data. The motion profile can comprise a path or pattern for the rotor 42 to travel within the gantry 34 to acquire the image data. For example, in order to acquire an image of the spine, the gantry 34 can move axially and along the spinal column to acquire images of the spine for 3D reconstruction. At block 214, the method can acquire image data along the motion profile. At block 216, the method can reconstruct the 3D volumetric image data 18 based on the acquired image data, and can output the image data 18 to the display device 32a or display device 20 at block 218. It should be understood that block 216 is merely exemplary, as the method could simply output the image data as a 2D image on the display device 32a or display device 20 if desired, without reconstructing a three-dimensional image.

At decision block 220, the method can determine if additional images are requested by the user 12 via the input device 32c. If additional images are requested, then the method can go to decision block 202. Otherwise, the method goes to decision block 222. At decision block 222, the method can determine if a power down request has been received via the input device 32c. If a power down request has been received, then the method can end. Otherwise, the method can loop to decision block 220.

Thus, the image acquisition control module 110 can be used to enable the user to acquire images of various portions of the patient's anatomy, including both soft tissue and hard or boney tissue. The use of both the multi-row detector 38 and the flat panel detector 40 within a single gantry 34 of an imaging system 16 enables these various images to be acquired with a single portable device. The collimator 37 can be controlled so that the shape of the x-rays emitted by the source 36 correspond with the selected one of the multi-row detector 38 and the flat panel detector 40, which can improve image acquisition. By employing both high contrast and low contrast imaging capabilities in a single device, the patient does not have to move between different imaging devices and the imaging can be performed in a single procedure.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

Figure 8:
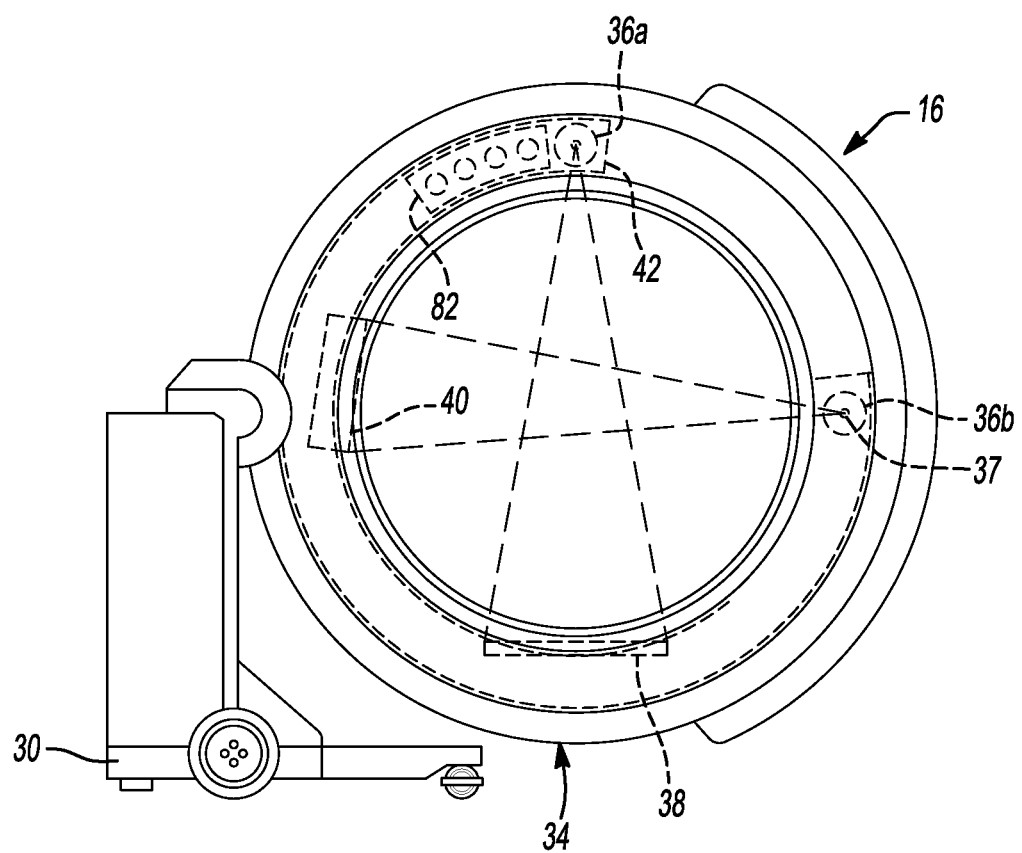
FIG. 8 is a schematic illustration of an exemplary imaging system including a first source aligned with a multi-panel detector and a second source aligned with a flat panel detector.

For example, while the imaging system 16 has been described herein as having a single source 36 diametrically opposed from the multi-row detector 38 and the flat panel detector 40, those of skill in the art will appreciate that the present disclosure, in its broadest aspects, may be constructed somewhat differently. In this regard, with reference to FIG. 8, an imaging system could include two sources 36a, 36b, one positioned diametrically opposed from the multi-row detector 38 and one positioned diametrically opposed from the flat panel detector 40. The sources 36a, 36b could be positioned about 90 degrees apart from each other, and the multi-row detector 38 and the flat panel detector 40 could be positioned about 90 degrees apart from each other.

What is claimed is:

1. A system for acquiring image data of a subject with an imaging system, comprising:
    a gantry that completely annularly encompasses at least a portion of the subject;
    a source positioned within and movable relative to the gantry, the source responsive to a signal to output at least one pulse;
    a multi-row detector positioned within and movable relative to the gantry, the multi-row detector positionable into alignment with the source to detect the at least one pulse emitted by the source and set multi-row detector data based on the detected at least one signal;
    a flat panel detector positioned within and movable relative to the gantry, the flat panel detector positionable into alignment with the source to detect the at least one pulse emitted by the source and set flat panel detector data based on the detected at least one signal; and
    an image acquisition control module that sets the signal for the source and determines only one of the multi-row detector and the flat panel detector to detect the at least one pulse emitted by the source.

2. The system of claim 1, wherein the image acquisition control module further comprises:
    an image control module that sets the signal for the source and receives the multi-row detector data and flat panel detector data, the image control module operable to reconstruct image data based on the multi-row detector data and flat panel detector data.

3. The system of claim 2, wherein the image control module receives user input data and determines which of the multi-row detector and the flat panel detector to use based on the user input data.

4. The system of claim 3, wherein the user input data further comprises a region of the patient for image acquisition or a type of detector to use for image acquisition.

5. The system of claim 4, wherein the source includes a first source and a second source within the gantry;
    wherein the multi-row detector is opposed to the first source;
    wherein the flat panel detector is opposed to the second source;
    wherein the first source is positioned and fixed about 90 degrees apart from the second source;
    wherein the multi-row detector is positioned and fixed about 90 degrees apart from and the flat panel detector.

6. The system of claim 3, further comprising a display, wherein the image acquisition control module outputs the reconstructed image data to the display.

7. The system of claim 1, wherein the image acquisition control module further comprises:
    a move control module that sets a move signal based on the determined one of the multi-row detector or the flat panel detector to move the multi-row detector or the flat panel detector into alignment with the source.

8. The system of claim 7, wherein the flat panel detector is movable relative to the multi-row detector based on the move signal set by the move control module.

9. The system of claim 1, wherein the gantry, source, multi-row detector and flat panel detector are mounted on a mobile cart.

10. The system of claim 1, wherein the source, multi-row detector and flat panel detector are coupled to a rotor positioned within and movable relative to the gantry.

11. The system of claim 1, further comprising:
    at least one tracking device coupled to a portion of the imaging system; and
    a navigation system that tracks the tracking device to determine a location of the portion of the imaging system.

12. A method for acquiring image data of a subject with an imaging system, comprising:
    providing a gantry operable to completely annularly encompass at least a portion of the subject, the imaging system including a source, a multi-row detector and a flat panel detector positioned within and coupled to a rotor movable relative to the gantry;
    receiving at least one user input that provides a request for acquiring image data of at least one of a soft tissue portion or a boney tissue portion of the subject;
    determining, based on the user input, only one of the multi-row detector and the flat panel detector to use to acquire the image data;
    moving the determined one of the multi-row detector and flat panel detector within the rotor into alignment with the source;
    outputting at least one pulse with the source;
    receiving the at least one pulse with the determined one of the multi-row detector and the flat panel detector; and
    outputting, based on the at least one pulse received by the detector, an image of the subject.

13. The method of claim 12, wherein outputting the image of the subject further comprises:
    reconstructing, based on the at least one pulse received by the detector, an image of the subject; and
    displaying the reconstructed image of the subject on a display.

14. The method of claim 13 wherein determining, based on the user input, which of the multi-row detector and the flat panel detector to use to acquire the image data further comprises:
    determining to use the multi-row detector to acquire image data of a low contrast region of the subject; and
    determining to use the flat panel detector to acquire image data of a high contrast region of the subject.

15. The method of claim 14, wherein determining to use the multi-row detector to acquire image data of the low contrast region of the subject includes inputting that the region of the subject includes the soft tissue portion of the subject;
    wherein determining to use the flat panel detector to acquire image data of the high contrast region of the subject includes inputting that the region of the subject includes the boney tissue portion of the subject.

16. The method of claim 15, wherein the determining, based on the user input, which of the multi-row detector and the flat panel detector to use to acquire the image data is automatically determined with an image control module.

17. The method of claim 14, moving the rotor having the source, the multi-row detector, and the flat panel detector positioned within and coupled to the rotor, 360° about an axis through the gantry.

18. The method of claim 12 wherein moving the selected one of the multi-row detector and flat panel detector into alignment with the source further comprises:
   moving the flat panel detector along an axis of the multi-row detector.

19. A method for acquiring image data of a subject with an imaging system, comprising:
   providing a gantry operable to completely annularly encompass at least a portion of the subject, the imaging system including a source, a multi-row detector and a flat panel detector positioned within and coupled to a rotor movable relative to the gantry;
   receiving at least one user input that provides a request for acquiring image data of a portion of the subject;
   determining, based on the user input, whether to use high contrast image acquisition or low contrast image acquisition to acquire the image data;
   moving the multi-row detector into alignment with the source to perform the low contrast image acquisition;
   moving the flat panel detector into alignment with the source to perform the high contrast image acquisition;
   outputting at least one pulse with the source;
   receiving the at least one pulse with the selected one of the multi-row detector and the flat panel detector;
   reconstructing, based on the at least one pulse received by the detector, an image of the subject; and
   displaying the reconstructed image of the subject on a display.

20. The method of claim 19, wherein providing the gantry further comprises:
   providing only one gantry to completely annularly encompass at least the portion of the subject, the source, the multi-row detector and the flat panel detector positioned within the gantry, the multi-row detector and flat panel detector movable relative to each other into alignment with the source.

21. The method of claim 19, wherein determining, based on the user input, whether to use high contrast image acquisition or low contrast image acquisition to acquire the image data further comprises:
   determining to use high contrast image acquisition or low contrast image acquisition based on a region of the patient for image acquisition; or
   determining to use high contrast image acquisition or low contrast image acquisition based on a type of detector selected by the user in the user input data.

22. The method of claim 21, wherein reconstructing, based on the at least one pulse received by the detector, an image of the subject includes reconstructing the image of the subject based on a multi-row detector data and a flat panel detector data from receiving the at least one pulse with the multi-row detector and the flat panel detector.

23. The method of claim 22, further comprising:
   operating the image acquisition control module to set a signal for the source and selecting, based on the user input, which of the multi-row detector and the flat panel detector to use to receive the at least one pulse with the selected one of the multi-row detector and the flat panel detector.

24. The method of claim 21 wherein reconstructing, based on the at least one pulse received by the detector, an image of the subject includes reconstructing a 3D volumetric image using algebraic technique where a theoretical image data projection of a theoretical patient is iteratively changed until the theoretical image data projection matches the acquired 2D projection image data.

25. The method of claim 24, generating forward 2D projections generated from the reconstructed 3D volumetric image data.

* * * * *